US008993551B2

(12) United States Patent
Ferguson et al.

(10) Patent No.: US 8,993,551 B2
(45) Date of Patent: Mar. 31, 2015

(54) COMPOSITION FOR THE REGULATION OF THE HUMAN IMMUNE SYSTEM AND THE PREVENTION AND TREATMENT OF DISEASES THEREOF

(76) Inventors: Alan Ferguson, Calgary (CA); John Charles Davidson, Calgary (CA)

( * ) Notice: Subject to any disclaimer, the term of this patent is extended or adjusted under 35 U.S.C. 154(b) by 365 days.

(21) Appl. No.: 12/715,515

(22) Filed: Mar. 2, 2010

(65) Prior Publication Data

US 2011/0059930 A1   Mar. 10, 2011

Related U.S. Application Data

(60) Division of application No. 11/361,982, filed on Feb. 27, 2006, now abandoned, which is a continuation-in-part of application No. 11/106,446, filed on Apr. 15, 2005, now abandoned, which is a continuation-in-part of application No. PCT/CA03/01451, filed on Sep. 24, 2003.

(30) Foreign Application Priority Data

Oct. 16, 2002 (CA) .................................... 2407429

(51) Int. Cl.
*A61K 31/05* (2006.01)
*A61K 31/56* (2006.01)
*A61K 31/202* (2006.01)
*A61K 31/557* (2006.01)
*A61K 31/575* (2006.01)

(52) U.S. Cl.
CPC ............. *A61K 31/202* (2013.01); *A61K 31/557* (2013.01); *A61K 31/05* (2013.01); *A61K 31/56* (2013.01); *A61K 31/575* (2013.01)
USPC ....................................................... 514/182

(58) Field of Classification Search
CPC ..... A61K 31/05; A61K 31/56; A61K 31/202; A61K 31/557; A61K 31/575; A61K 2300/00
See application file for complete search history.

(56) References Cited

U.S. PATENT DOCUMENTS

| 6,048,846 | A  | 4/2000 | Cochran |
| 6,063,776 | A  | 5/2000 | Ostlund, Jr. |
| 6,110,471 | A  | 8/2000 | Conti et al. |
| 6,677,327 | B1 | 1/2004 | Gottemoller |
| 2002/0048613 | A1 | 4/2002 | Romanczyk et al. |
| 2004/0001817 | A1* | 1/2004 | Giampapa .................... 424/94.1 |
| 2006/0110465 | A1 | 5/2006 | Hashmi et al. |

FOREIGN PATENT DOCUMENTS

| CA | 2382262 | 12/2004 |
| CA | 2419249 | 3/2007 |
| EP | 0882450 | 12/1998 |
| JP | 11346711 A * | 12/1999 |
| JP | 2001278792 A * | 10/2001 |
| JP | 2002138295 | 5/2002 |
| WO | WO9717976 | 5/1997 |
| WO | WO0007604 | 2/2000 |
| WO | WO0038699 | 7/2000 |
| ZA | 200002342 A * | 3/2001 |

OTHER PUBLICATIONS

Alternative Medicine Review, Plant Sterols and Sterolins vol. 6, No. 6, No. 2, 2001, Plant Sterols and Sterolins.
Cheung et al; Lancet 2002; 360: 1831-37.
Signet_FMC Avicel cellulose in capsule formulations.pdf, (2002).
"Welcome to the Sterol117 TM website" CELT Corporation 2002-2003, Online! XP002266849 Retrieved from the Internet: <URL:www.sterol117.com> 'retrieved on Jan. 14, 2004!.
Senthilmohan Senti T et al: "Superoxide radical scavenging ability of bioflavonoids" Free Radical Biology and Medicine, vol. 31, No. 10, Nov. 2001, p. S38 XP002266850 8th Annual Meeting of the Oxygen Society; REsearch Triangle Park, North Carolina, USA; Nov. 15-19, 2001 ISSN: 0891-5849.
Database Medline 'Online! US National Library of Medicine (NLM) Bethesda, MD, US; Apr. 2001 "Monograph. Plant sterols and sterolins." Database accession No. NLM11302782 XP002267332 abstract.
Naturopathic Wisdom Notes, 'Online! vol. 9, No. 1, Jan. 2003, pp. 1-6, XP002266852 Retrieved from the Internet: <URL:www.goldrvr.island.net/{ipincott/jan_feb03.htm> 'retrieved on Jan. 14, 2004! p. 5, paragraph 3.

* cited by examiner

*Primary Examiner* — Sarah Pihonak
(74) *Attorney, Agent, or Firm* — Michael R. Williams; Ade & Company Inc.

(57) ABSTRACT

A nutritional supplement composed of phytosterols, antioxidants, and other complexes, including essential fatty acids, amino acids, peptides, proline rich polypeptides and digestive enzymes is described. The nutritional supplement may be used by individuals suffering from or at risk of developing immune system diseases; breast cancer, colon and prostate cancer; HIV infection; high cholesterol; or enlarged prostate. In the preferred form, the invention comprises phytosterols and antioxidants, together with essential fatty acids derived from amino acids, short chain peptides, proline rich polypeptides and digestive enzymes, and a microcellulose filler.

3 Claims, No Drawings

COMPOSITION FOR THE REGULATION OF THE HUMAN IMMUNE SYSTEM AND THE PREVENTION AND TREATMENT OF DISEASES THEREOF

PRIOR APPLICATION INFORMATION

This application is a divisional of U.S. patent application Ser. No. 11/361,982, filed Feb. 27, 2006, which is a continuation-in-part of U.S. patent application Ser. No. 11/106,446, filed Apr. 15, 2005, which is a continuation-in-part of International Application PCT CA03/01451, filed Sep. 24, 2003 which in turn claims the benefit of Canadian Patent Application 2,407,429, filed Oct. 16, 2002.

FIELD OF THE INVENTION

This invention relates to the field of nutritional supplements.

BACKGROUND OF THE INVENTION

Phytosterols are fats that are present in all plants, including fruits and vegetables. Although structurally similar to cholesterol, the sterols synthesized by animals and plants differ in the nature of their side chain (see FIG. 1) (Allayee et al. 2000, Science 290: 1709-1711).

In animals, cholesterol is the most abundant sterol. In plants, more than 40 sterols have been identified, of which beta-sitosterol, stigmasterol, and campesterol are the most common (Hicks and Moreau 2001, Food Technol 55: 63-67). These phytosterols occur in free form or are esterified to free fatty acids, sugar moieties or phenolic acids (Baker et al. 1999, Food Chem Toxicol 37: 13-22). Studies have demonstrated that beta-sitosterol possesses anti-inflammatory and immune modulating properties. It has been estimated that consumption of 3 g/day of phytosterols could reduce the risk of heart disease by 15% to 40%, depending on age and other dietary factors (Hicks and Moreau 2001). However, the western diet typically contains 100-300 mg of plant sterols (Nguyen 1999, J Nutr 129: 2109-2112).

Enzogenol™ is an example of a water soluble extract of monomeric and oligomeric proanthocyanidins, flavonoids, flavonoid glycosides, esters and natural organic acids prepared from the bark of Pinus radiate by a pure water extraction process (Shand et al. 2003, Phytother Res 17: 490-494). The extract has been shown to have in vitro antioxidant action as measured by inhibition of micelle oxidation, red blood cell hemolysis and a nitro blue tetra zolium enzymatic method (Gieseg and Baird 1998, Free Rad Biol Med 25: S104; Wood et al. 2002, Food Chem 77: 155-161).

Omega 3, 6 and 9 fatty acids, such as found in Cellasate, have a structural role in phospholipids of all cell membranes in the body, influencing membrane viscosity and permeability (Drevon 1992, Nutr Rev 50: 38-45). Eicosapentaenoic acid (EPA) and docosahexaenoic acid (DHA) are thought to be responsible for beneficial effects, such as prevention and management of coronary heart disease and hypertension (Simopoulos 1999, Am J Clin Nutr 70: 560S-569S).

SUMMARY OF THE INVENTION

According to a first aspect of the invention, there is provided a method of modifying blood lipid parameters comprising administering to an individual in need of such treatment an effective amount of a composition comprising:
  10% to 90% phytosterols;
  5% to 85% essential fatty acid complexes; and
  5% to 85% antioxidants.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As used herein, the term "treating" in its various grammatical forms refers to curing, reversing, attenuating, alleviating, minimizing, suppressing or halting the deleterious effects of a disease state, disease progression, disease causitive agent or other abnormal condition.

Described herein is a new composition or nutritional supplement composed of natural products. In some embodiments, the supplement may be used by individuals desirous of regulating their immune system, for example, to prevent and treat diseases thereof. As discussed below, the composition combines phytosterols with anti-oxidants and fatty acid complexes.

The composition has also been demonstrated to be beneficial in the modification of blood lipid parameters, as discussed below. Specifically, the composition or supplement has been shown to reduce the total cholesterol (TC) to high density lipoprotein (HDL) ratio (TC/HDL) as well as to reduce the low density lipoprotein (LDL) to HDL ratio (LDL/HDL) compared to a placebo-treated control, as discussed below. As will be appreciated by one of skill in the art, the composition or supplement at formulae and/or dosages described herein is in some embodiments of the invention administered to an individual in need of such treatment or used for modifying the blood lipid parameters of said individual, for example, reducing the TC/HDL ratio or reducing the LDL/HDL ratio. As will be appreciated by one of skill in the art, examples of such individuals include but are by no means limited to individuals having, at risk of having or suspected of having hypercholesterolemia or otherwise having or suspected of having elevated cholesterol levels or reduced HDL levels.

As discussed below, administration of the composition or supplement to an individual in need of such treatment reduced basophil and IL-6 levels in said individual compared to a second individual administered a placebo control.

In another embodiment, administration of the supplement as described herein to an individual in need of such treatment reduced LDL levels, increased HDL levels, reduced the LDL/HDL ratio or reduced the total cholesterol to HDL ratio in said individual compared to a second individual administered a placebo control.

In one embodiment, the composition or supplement comprises: 10% to 90% phytosterols, 5% to 85% essential fatty acid complexes and 5-85% antioxidants. In other embodiments, the supplement comprises 20% to 90% phytosterols, 5% to 75% essential fatty acid complexes and 5-75% antioxidants. In another embodiment, the composition or supplement comprises: 10% to 80% phytosterols, 10% to 80% essential fatty acid complexes and 10-80% antioxidants. In other embodiments, the supplement comprises 20% to 80% phytosterols, 10% to 80% essential fatty acid complexes and 10 to 80% antioxidants. In a preferred embodiment, the supplement comprises 29% to 75% phytosterols; 10% to 50% essential fatty acid complexes; and 5% to 50% antioxidants. The supplement or composition may be arranged in the form of a capsule or other suitable, ingestible format, such as a tablet, pill or other similar form known in the art.

In a preferred embodiment, the supplement or composition comprises 29% to 75% beta-sitosterol; 10% to 50% essential fatty acid complexes; and 5% to 50% antioxidants.

In a yet further preferred embodiment, there is provided a single-dose supplement or composition comprising: 300 mg phytosterols; 50 mg essential fatty acid complexes; 20 mg antioxidants; and 30 mg micro-cellulose filler. As discussed herein, this composition may be taken once daily or twice daily.

In some embodiments, the above-described compositions are used for treating, preventing or ameliorating symptoms associated with an immune system disease. In these embodiments, the composition or supplement at a dosage, concentration or range described above is administered to an individual in need of such treatment. Examples of immune system diseases include but are by no means limited to colds, flu, diabetes, allergies, asthma, pneumonia, fibromyalgia, HIV infection, hepatitis C infection, and multiple sclerosis. In a preferred embodiment, the composition at dosages, concentrations or ranges described above is used to treat or prevent pneumonia, fibromyalgia or a hepatitis C infection. In a yet preferred embodiment, the composition or supplement described above is used to treat an immune system disease as described above by administering the composition at a concentration or dosage as described to an individual in need of such treatment.

Accordingly, in yet another embodiment, there is provided a method of decreasing the LDL/HDL ratio or reducing the TC/HDL ratio in an individual in need of such treatment comprising administering to said individual an effective amount of a supplement comprising 10% to 90% phytosterols, 5% to 85% essential fatty acid complexes and 5-85% antioxidants. In other embodiments, the supplement comprises 20% to 90% phytosterols, 5% to 75% essential fatty acid complexes and 5-75% antioxidants. In another embodiment, the composition or supplement comprises: 10% to 80% phytosterols, 10% to 80% essential fatty acid complexes and 10-80% antioxidants. In other embodiments, the supplement comprises 20% to 80% phytosterols, 10% to 80% essential fatty acid complexes and 10 to 80% antioxidants. In a preferred embodiment, the supplement comprises 29% to 75% phytosterols; 10% to 50% essential fatty acid complexes; and 5% to 50% antioxidants. In a further preferred embodiment, the supplement or composition comprises 29% to 75% beta-sitosterol; 10% to 50% essential fatty acid complexes; and 5% to 50% antioxidants. In a yet further preferred embodiment, there is provided a single-dose supplement or composition comprising: 300 mg phytosterols; 50 mg essential fatty acid complexes; 20 mg antioxidants; and 30 mg micro-cellulose filler. As discussed herein, this composition may be taken once daily or twice daily.

The inherent ingenuity of the invention is the discovery of the range of the amount of beta-sitosterol that is the most effective to achieve the goal of regulating the Human Immune System and the prevention and/or treatment of diseases thereof. As a result, this new composition need only be taken once a day to maintain general health.

The further uniqueness of the invention is the discovery that combining phytosterols with anti-oxidants and fatty acid complexes produces a synergistic effect whereby the cumulative total effect of the composition is greater than the sum of the individual effects of the respective components. As a result, this new composition optimizes the immune system to deal with viral and bacterial infections, while also protecting the body from degeneration due to free radical damage.

Additionally, the invention is original and novel because it can not only assist in preventing possible causes of cancer, but, it inhibits or reduces cancer cell growth in breast, colon and prostate cancer cases, and facilitates the removal of the dead tissue arising from the death of the said tumors. That is, the composition can modulate or optimize, as opposed to only boosting, the immune system, as discussed below.

The utility of said invention is further demonstrated and confirmed by the fact that it accomplishes its goals with none of the physical or psychological side effects of traditional treatments such as radiation, chemotherapy and surgery.

The basis of the present invention is the use of a combination of phytosterols, anti-oxidants and fatty acid complexes for the following purposes:

1. To modulate the Human Immune System;
2. To prevent or treat diseases of the Human Immune System, for example but by no means limited to:
   Common cold and flu;
   Microorganism infections, for example viral, yeast and bacterial infections;
   Allergies;
   Rheumatoid Arthritis;
   Lupus;
   Chronic Fatigue Syndrome;
   Fibromyalgia;
   Asthma;
   Diabetes; and
   Eczema.
3. To inhibit or reduce cancer cell growth in breast, colon and prostate cancer cases;
4. To maintain CD4 Lymphocyte counts in HIV patients;
5. To treat enlarged prostate problems;
6. As an anti-inflammatory agent; and
7. Modifying blood lipid parameters, as discussed below.

As discussed above, the compositions described herein act to modulate the immune system. Specifically, the compositions act to restore normal functions in an individual in need thereof. As will be apparent to one of skill in the art, this explains how the compositions are able to treat diseases or conditions characterized by immune activation, such as autoimmune disorders such as arthritis and inflammation, as well as diseases characterized by immune suppression or deficiency, such as acquired immune deficiency syndrome. While not wishing to be bound to a specific theory, the inventors believe that the composition acts to modulate immune function such that an immune system that is acting abnormally, that is, is either depressed or chronically activated, returns to normal functioning, that is, returns to the state of activation found in most individuals who are not currently undergoing a challenge to their immune system.

Although preferred compositions to achieve these ends are listed below, they are by no means to be interpreted as limiting the broad scope of the present invention as various other combinations of phytosterols, anti-oxidants and fatty acid complexes may achieve the same beneficial results.

The preferred composition of the present application consists of 400 mg capsules containing 300 mg of phytosterols (a minimum of which is 117 mg of beta-sitosterol), 50 mg essential fatty acid complexes, 20 mg broad spectrum anti-oxidants, and 30 mg micro-cellulose filler. As will be appreciated by one of skill in the art, this represents an example of an effective amount of the composition. Other suitable concentrations and dosages may be determined using the ranges described herein. As will be apparent to one of skill in the art, as used herein, "effective amount" refers to an amount that achieves the desired effect.

In another preferred form, the composition comprises from 29% to 75% beta-sitosterol, 10% to 50% essential fatty acid complexes and from 5% to 50% antioxidants. As will be appreciated by one of skill in the art, other suitable, pharmaceutically acceptable fillers may also be used in the invention.

In other embodiments, there is provided a composition comprising: 1-95% phytosterols; 1-95% essential fatty acid complexes; and 1-95% antioxidants. The composition may further include 1-95% filler, for example, micro-cellulose filler. In other embodiments, 5-95% of the phytosterols may be beta-sitosterol.

A further innovative feature of the invention is the discovery that the essential fatty acid complexes together are not only themselves an immune system modulator, but also facilitates the body's absorption of beta-sitosterol and antioxidants.

This invention is a composition of natural products that is designed to stimulate the body to marshal its own natural defenses against allergies and other immune related disorders, breast, colon and prostate cancer, and AIDS, as opposed to alleviating or preventing these disorders with chemical or synthetic products. Many of the traditional treatments have severe side effects, which in the case of prostate cancer can include impotence and incontinence, and in the case of chemotherapy, severe depression of the immune system. Traditional treatments also only treat the tumors, i.e. the symptoms, and not the underlying cause, and in the case of chemotherapy, leave dead tissue to be removed from the body.

One of the suspected causes of cancer is free radical damage on cellular components such as DNA or the cell membranes. Free radicals are the natural by-products of many processes within and among cells. They are also created by exposure to various environmental factors such as tobacco smoke and radiation. Once formed these highly reactive radicals can start a chain of reactions that can result in damage to cell walls, certain cell structures, and the genetic material within the cells such as DNA.

In the preferred form this composition contains one of the world's most advanced anti-oxidant complexes, Enzogenol™, produced by Enzo Nutraceuticals through a patented process that creates an aqueous extract from Pinus Radiata (pine bark), which is a superior source of proanthocyanidins and flavonoids. This technically advanced anti-oxidant complex provides an excellent source of free radical scavengers:

In addition to scavenging free radicals, the Enzogenol™ in this composition can stimulate phagocytosis, an immune system response in which cells ingest and eliminate harmful micro-organisms and foreign heavy metals, and hence facilitates the removal of the by-products of cell death.

Research has shown that the Human Immune System can be stimulated by beta-sitosterol. This composition contains this remarkable phytonutrient which has been shown to be effective in inhibiting cancer cell growth and accelerating cancer cell death in breast, prostate and colon cancer. It can also reduce metastases to lymph nodes.

Research at the University of New York at Buffalo by Awad, Downey and Fink has shown that beta-sitosterol can inhibit breast cancer cell growth by 66% after 3 days and 80% after 5 days. It can also increase the rate of cell death by 600% (Int. J. Mol. Med 2000 May 5(5)). Research by the same group has also shown that beta-sitosterol can inhibit prostate cancer cell growth by 24% and increase cell death by 400% (Nutr Cancer 1998; 32 (1)). Similar research on colon cancer cells showed a reduction in cell growth of 55% (Anti Cancer Res, 1998 Mar.-Apr. 18 (2a)). The exact mechanism behind the inhibition of cancer cell growth and the increase in apoptosis is not yet fully understood, but may be related to the increase in T-cell proliferation produced by beta-sitosterol (Int. Jnl. Immuno Pharmacol 1996 vol 18 Bouic et al). Beta-sitosterol has been shown to maintain CD4 lymphocyte count in AIDS patients (AIDS Bulletin Summer 97).

The potential benefits of the antioxidants together with the beta-sitosterol to scavenge free radicals and to kill and remove tumors can only be realized if the human body actually absorbs both the anti-oxidant complex and the betasitosterol. The role of the essential fatty acid complex is to ensure that the antioxidant complex and the beta-sitosterol are absorbed. The essential fatty acid complex itself is a blend of essential fatty acids, amino acids, praline rich peptides, short chain polypeptides and enzymes. This complex also happens to be an immune system modulator, and consequently also supports the body's attack on cancer by promoting and supporting the T-cell proliferation initiated by the beta-sitosterol.

The combined effects of the antioxidant complex, the beta-sitosterol and the essential fatty acid complex on breast, colon and prostate cancers are to reduce the risk of the formation of new cancers through the more effective scavenging of free radicals, to inhibit the growth and increase the rate of cell death of the tumors, and to assist the body in disposing of dead tumor cells.

This formulation has been used to treat a 68 year old male with a PSA of 17. Over a six month period his PSA, (the normal measure of prostate cancer which would normally increase over time), dropped to 11.8, a reduction of over 30%, with no side effects.

The combined immune modulating properties of beta-sitosterol, antioxidant complex, and the essential fatty acid complex also make this formulation an excellent anti-allergen with no side effects which is also new and unique in the field of anti-allergens. This formulation has been used to treat several adults with ages ranging between 22 and 52 with excellent results occurring in the space of five to six days, again with none of the side effects normally associated with anti-allergens.

Early trials of this unique formulation have also shown the capacity to alleviate such immune related disorders as rheumatoid arthritis, again with none of the adverse side effects normally associated with the remedies traditionally used in this area.

In addition, the effectiveness of beta-sitosterol in maintaining the CD4 lymphocyte count in AIDS patients can be increased by the addition of the antioxidant and essential fatty acid complexes in this formulation, again providing an important new application for this new and unique formulation.

Normally capsules are taken once a day, in a preferred embodiment, at least one hour or at least half an hour before and at least 2 hours after food, with water or fruit juice (NOT milk or any other fat containing liquid). As will be appreciated by one of skill the art, these time frames and frequencies are suggested for most users, but other users may find best results taking the capsule more frequently or less frequently, or, for example, with meals or closer to meals.

The term "phytosterols" is to be construed to include, but not to be restricted to, beta-sitosterol, stigmasterol, campesterol, brassicasterol together with their associated glucosides.

The term "antioxidant complex" is to be construed to include, but not to be restricted to, a broad range of proanthocyanidins, flavonoids and polyphenols.

The term "essential fatty acid complex" is to be construed to include, but not restricted to, amino acids, essential fatty acids, peptides, proline rich poly peptides, and various digestive enzymes.

The following are examples of usages, showing the utility of the composition.

Example 1

Allergies

The composition was used by an individual to treat seasonal allergies. The individual found that one or more of the symptoms associated with allergies, including runny nose, red itchy eyes, aching joints and a feeling of always being tired, were ameliorated following taking the composition. Specifically, users found that the symptoms were ameliorated after 24 hours and remained symptom free after 2 weeks by taking one dosage or capsule per day.

Another individual who suffered from moderate asthma and allergies to dust and animal hair found that taking the composition relieved or ameliorated symptoms including itchy and watery eyes and a runny nose. This individual also reported increased energy and an improved sense of well-being.

Another individual who suffered from allergies to dust mites which led to a chronically stuffed nose that would drip constantly found that these symptoms were ameliorated following taking the composition over an initial regimen and then taking the composition daily on an as needed basis.

Another individual reported allergies to pollen and other seasonal allergies and found that taking the composition over a period of a few weeks ameliorated the allergy-related symptoms, including itchy eyes and sneezing.

Example 2

Asthma

An individual who suffered from asthma found that following taking the composition regularly for 3 months, the asthma-associated symptoms were ameliorated.

Another individual who suffered from asthma and food allergies and had symptoms including itchy eyes and a runny nose found that within 2 weeks of taking the composition on a regular basis, she was off the antihistamines and her stuffy nose was completely gone. Furthermore, she found that her asthma progressively improved and was able to eat foods that she couldn't eat before without having immediate allergic reactions.

Example 3

Cold & Flu

One individual who had contracted pneumonia took two capsules of the composition per day over a five day period and found that the symptoms associated with pneumonia were ameliorated.

Another individual who also had a cold develop into pneumonia found that the symptoms associated with the illness were ameliorated during a two month regimen of taking the composition daily.

Another individual took the composition regularly to prevent colds or "flu". This individual found less frequent occurrences of colds and "flu" and also found that taking the composition on a regular basis provided "an all over feeling of wellbeing".

Example 4

Diabetes

A diabetic who was using insulin 3 times per day for the last 12 years, at an average of 50 units a day pf insulin, consisting of 20 units in the morning, 20 units in the afternoon and 10 units before bed found that after having taken the composition daily for 3 weeks that the individual was able to eliminate the night-time units.

Example 5

Eczema

An individual who suffered from eczema, particularly under her armpits on both sides, would also get eczema on her hands whenever her hands were exposed to any chemicals or detergents (ie doing any cleaning) and even after folding the laundry. She managed the eczema with cortisone cream—a few times per week. After 2 months of taking the composition along with eliminating certain food allergies, her eczema was 90% gone (in places where it had been chronic for years) and her hands (which used to be effected almost constantly) were completely clear.

Example 6

Fibromyalgia

An individual who suffered from fibromyalgia found that taking one dose of the composition one hour before breakfast helped ameliorate symptoms including pain and insomnia.

Another individual with fibromyalgia reported wakening 3-4 times per night with severe cramps in their feet and calves. Following taking the composition on a regular dosage regimen, this individual found amelioration of many of the symptoms associated with the fibromyalgia.

Example 7

Hepatitis C

An individual who suffers from hepatitis C reported a progressive increase in energy during the first 2 weeks of taking the composition.

Example 8

HIV

An individual having an HIV infection reported that their CD-4 level climbed by 300 points following a 3 month regimen of taking the composition.

Example 9

Multiple Sclerosis

An individual with multiple sclerosis reported increased energy and improved balance on taking the composition.

Example 10

Urinary Flow

An individual suffering from prostate enlargement reported that following taking the composition, the time between urinations was increased and also reported increased flow.

Example 11

Pelvic Inflammatory Disease

Several users have reported that the composition as described above alleviated one or more of the symptoms associated with pelvic inflammatory disease.

Example 12

Rheumatoid Arthritis

An individual with rheumatoid arthritis reported that following taking two capsules of the composition per day for two weeks, many of the symptoms associated with the rheumatoid arthritis were ameliorated.

Dosage and Administration

The recommended adult dosing regimen is currently one capsule per day by oral ingestion. In most embodiments, the supplement is taken with water or juice (not milk), on an empty stomach 45 minutes before eating. One capsule a day normally maintains general health. More serious conditions may require two capsules per day, one in the morning and one at night. The dosing regimen can be changed, for example, to two capsules per day for the first week, followed by one capsule per day.

Pharmacology

Phytosterols:

Beta-sitosterol is not synthesized endogenously in mammals. Animal studies have demonstrated its intestinal absorption in mammals is minimal, possibly as little as 5% of total dietary beta-sitosterol consumed. In contrast, intestinal absorption of cholesterol is 45-54% of intake. Unlike cholesterol, beta-sitosterol is secreted into the bile and is esterified outside the intestinal wall at a much slower rate. After secretion into the bile, beta-sitosterol is stored in the gallbladder, then released intermittently into the duodenum, and subsequently incorporated into feces.

It has been proposed that phytosterols inhibit the uptake of dietary and endogenously produced cholesterol from the gut, causing a decrease in serum cholesterol levels (Nguyen 1999). One theory suggests that cholesterol in the intestine, already marginally soluble, is precipitated into a non-absorbable state by the presence of added phytosterols (Hicks and Moreau 2001). A second theory proposes that cholesterol must enter bile salt and phospholipid containing "mixed micelles" to be absorbed into the bloodstream. Cholesterol is only marginally soluble in these micelles and is displaced by phytosterols, preventing its absorption (Hicks and Moreau 2001). Due to the limited capacity in the micelles for carrying cholesterol, compounds with similar structures, such as plant sterols, can compete with cholesterol for this space. Therefore, increasing the amounts of plant sterols may result in less cholesterol in mixed micelles and hence, decreased absorption of cholesterol from the gut.

Orally ingested flavonoids are largely present as aglycons in the intestine and become absorbed with micelles of bile acids into the epithelium and then into the blood. Through the portal vein, the major part of the flavonoids would be delivered to the liver, which decomposes them (Haysteen 1983, Biochem Pharmacol 32: 1141-1148).

Both EPA and DHA have been found to alter plasma membrane composition, cell-signaling mechanisms, eicosanoid responses, cytokine release, and immune cell responses (Arslan et al, 2002, Lipids 37: 935-941). One mechanism for these effects may be that EPA and DHA are incorporated into membrane phospholipids by replacing arachidonic acid (AA, n-6 fatty acid). AA is the substrate for the synthesis of eicosanoids, such as fluomboxane A2 and prostaglandin E2 (O'Morain et al. 1990, Scand J Gastroenterol 31: 267-272). N-3 fatty acids have a greater affinity for the cycle- and lipoxygenase enzymes than n-6 fatty acids and they competitively inhibit the formation of prostaglandins and leukotrienes (Drevon 1992). Therefore, increased dietary intake of n-3 fatty acids may shift the balance of the eicosanoid production to a less inflammatory profile (Arslan et al. 2002). Another mechanism for the effect of n-3 fatty acids is associated with the change in fluidity by incorporation of fatty acids in the cell membranes and an influence on the activities of membrane-associated enzymes or receptors (Vognild et al. 1998, Lipids 33: 427-436).

This study was designed to investigate whether supplementation with the above-described supplement comprising plant sterols, antioxidants and essential fatty acids could, in subjects with non-food allergies:

a) Decrease immunological response to allergens
b) Beneficially modify blood lipid parameters Subjects Twenty subjects consisting of 16 females and 4 males, aged from 20-50, and who fit specific inclusion/exclusion criteria were recruited. The inclusion/exclusion criteria were as follows:

Inclusion Criteria:

Male and female subjects aged 18 years or older

For females, confirmation (via pregnancy test) of non-pregnancy at baseline, and use of acceptable birth control method in females of childbearing potential No food allergies Willing and able to give informed written consent Exclusion Criteria:

Pregnancy/breast feeding

History of clinical significant and unstable cardiovascular, pulmonary, renal, neurological dermatological, hepatic or endocrine disease in the past 6 months Change in medication 4 weeks before entry into study History of frequent respiratory infections Diabetes or immune disorder such as lupus erythematosis or HIV/AIDS Known allergy to the supplement or any of its components History of drug, alcohol or substance abuse in the past 6 months Participation in any clinical trial within 6 weeks preceding day 1 of the study All participants were recruited from the University of Guelph or the City of Guelph. At the study screening, participants were given a letter of information and the consent form to sign. Respondents received a verbal briefing of the study protocol and the same information in writing. They signed an informed consent and completed a questionnaire to ensure compliance with the inclusion/exclusion criteria.

All participants were questioned on the nature of their allergies. Eligible subjects were required to have non-food allergies, but were required to have allergies to dust, animal dander, animal saliva, molds, etc. In addition, the study required that all subjects had received an allergy test by their physician to verify allergen response, or had been prescribed medication in the past to treat their allergies.

Experimental Design

This study was conducted as a double blind, placebo-controlled clinical trial. Subjects in the treatment group consumed two capsules of the above-described supplement for the first seven days in order to reach phytosterol threshold levels, followed by a maintenance dosage of 1 capsule per day. In these experiments, each capsule contained 300 mg of phytosterols (117 mg of β-Sitosterol) derived from soy, 20 mg of Enzogenol™ (antioxidants) extracted from pine bark, and 50 mg of Cellasate™ (a mixture of proteins and essential fatty acids) from seeds and fish oils, although as will be appreciated by one of skill in the art, other suitable formulations as discussed above may also be used. These include embodiments wherein the composition or supplement comprises: 10-90% phytosterols, 5-85% essential fatty acid complexes, and 5 to 85% antioxidant; or 29% to 75% phytosterols; 10% to 50% essential fatty acid complexes; and 5% to 50% antioxidants as well as embodiments wherein the supplement or composition comprises 29% to 75% beta-sitosterol; 10% to 50% essential fatty acid complexes; and 5% to 50% antioxidants as well as other embodiments described herein.

The placebo consisted of a rice flour mixture, identical in appearance to the supplement, and the consumption pattern for the placebo was the same for the placebo group as for the treatment group. The supplement and placebo supplementation phase lasted 28 days.

Subjects were required to visit the HNRU human clinical testing unit on three separate occasions. Subjects came in for baseline testing (day 0) and returned on day 7 of the study and again on day 28, the last day of the study. On the initial visit, height, weight and a blood sample were taken. Blood was analyzed for complete blood cell count (CHC), plasma DHEA, Cortisol, total HDL and LDL-cholesterol concentrations, and triglycerides. A Quantikine high sensitivity Elisa kit was used in order to measure human IL-6 in the plasma collected. Throughout the study, subjects were required to complete a daily journal listing specific allergy symptoms, non-allergy symptoms and any medications taken during the supplementation phase.

RESULTS

Immune Parameters
Basophils

The effects of the supplement on immune parameters are presented in Table 1. A number of studies support the belief that human basophils play an important role in allergic inflammation. Mast cells and basophils express the high affinity receptor for IgE (FcepsilonRI) and play a central role for IgE-associated immediate hypersensitivity reactions and allergic disorders. During allergic reactions, basophils migrate from the blood compartment to inflammatory sites, where they act as effector cells in concert with eosinophils. Basophils release histamine during inflammation and allergic reactions.

The participants in the treatment group, when compared to the control group, showed a significant reduction in basophil count, while the reduction seen in the control group was non-significant. A reduction in basophil count may indicate a reduction in histamine release.

Interleukin-6

The immune system also responds to stressors by causing certain immune cells to secrete the pro-inflammatory cytokines, Interleukin-1 (IL-1) and Interleukin-6 (IL-6). These cytokines are both involved in inflammation and IL-6 in particular is thought to worsen the symptoms of autoimmune diseases and fibromyalgia. Interleukin-6 has been found to act as a growth factor in several tumors and some viruses also use IL-6 to replicate. Interleukin-6 also causes calcium to be released from bone, promoting osteoporosis. We must control the release of these cytokines if we want to enhance immunity and reduce degenerative diseases.

It was noted in the pilot trial that the pro-inflammatory cytokine IL-6 levels showed a substantial reduction in the treated group when compared to the control group.

The supplement has demonstrated that it has an effect on histamine-containing basophil counts and a reduction of IL-6 levels, and consequently may substantially alleviate symptoms associated with airborne allergens, asthma and allergic rhinitis.

Cortisol/DHEA Levels

The body has developed mechanisms to protect it from the damaging effects of stress. The "fight-or-flight" response is one way the body deals with extreme situations of stress. Upon realizing we are in danger, the brain sounds an alarm, telling our adrenal glands to secrete adrenaline and cortisol, which mobilizes the body to fight or run. This response is supposed to be a short-lived reaction yet today most of us are in and out of this state continually. As a result, our immune system becomes imbalanced, sending out too many inflammatory cytokines. Our adrenal glands become exhausted, weakening several body systems, especially the cardiovascular and endocrine systems.

DHEA is an abbreviation for dehydroepiandrosterone. It is a hormone made primarily by the adrenal or stress glands. Hormones are messenger molecules that influence the function of cells and tissues all over the body. DHEA and cortisol are the body's long-acting stress hormones and are antagonistic to each other to some degree. Whereas DHEA has an anabolic or building influence, cortisol has a catabolic or tearing down effect on the body. Both of these effects are essential and these two hormones must be in proper balance for optimal health. How do these hormones become imbalanced?

By stress maladaptation. Stress maladaptation is the body's inappropriate response to prolonged stress. The normal reaction of the body to stress is to produce greater quantities of both cortisol and DHEA. When the stress is gone, the body reduces its output of cortisol and DHEA to resting levels and everything is fine. This is what happens with short episodes of stress. However, when the stress is prolonged, the body prefers to make increasingly greater amounts of cortisol and less DHEA. How long does it take for this to occur?

One study showed that after just 28 days of continuous stress cortisol levels had climbed to 240 percent of starting values and DHEA had dropped to 15 percent of initial levels. What's even worse is that even after the stress is removed, the body sometimes does not recover and bring these hormones back to normal levels, but instead, remains in the stress response mode with high cortisol and low DHEA output. The consequences of elevated cortisol and reduced DHEA levels are devastating: the immune system is compromised with increased risk to infections, certain cancers, allergies and autoimmune diseases.

A tremendous body of research has shown that when cortisol goes up, DHEA drops and when DHEA is normal, cortisol also normalizes. Low DHEA levels are seen in those that are immune compromised, have arteriosclerosis (hardening of the arteries), diabetes and lupus.

Cortisol helps the body maintain homeostasis in the face of stressors, counteracts inflammatory and allergic reactions and controls the metabolism of protein and carbohydrates.

Cortisol is a very misunderstood hormone. Balance is the key. In naturally low doses, it stimulates the immune system and in high doses, as prescribed in synthetic drug form, it can be immune suppressing. Remember that cortisol plays a role in counteracting inflammatory responses in the immune system and when cortisol is not available because the adrenal glands have become exhausted from too much stress, inflammation is allowed to continue unchecked. Conversely, too much cortisol and you have immune suppression.

In the conventional standard of care, any cortisol level within a very broad range is considered normal, and anything outside that range indicates disease. Cortisol production has an ACTH dependant circadian rhythm with peak levels in the early morning and a nadir at night (salivary cortisol ranges can vary from 8.0 to 1.0 in the morning and 1.0 to 0.1 in the evening) The factor controlling this rhythm is not completely defined and can be disrupted by a number of physical and psychological conditions. ACTH and cortisol are secreted independent of circadian rhythm in response to physical and psychological stress.

In the early stages of adrenal stress, cortisol levels will be too high during the day and continue rising in the evening. This is called "hyperadrenia". In the middle stages, cortisol may rise and fall unevenly as the body struggles to balance itself despite the disruptions of caffeine, carbs and other factors, but levels are not normal and are typically too high at night. In advanced stages, when the adrenals are exhausted from overwork, cortisol will never reach normal levels ("hypoadrenia").

None of the participants in the trial were known to have any of the autoimmune diseases that are associated with elevated cortisol levels. The change in cortisol levels noted in the pilot trial appear to be in the normal range, and neither DHEA nor cortisol levels, nor the ratio of these two parameters, showed significant changes at the pa0.05 level.

Cardiovascular Parameters

The effects of the supplement on lipid and lipoprotein parameters are illustrated in Table 2 and Table 3.

Cholesterol is an extremely important biological molecule that has roles in membrane structure as well as being a precursor for the synthesis of the steroid hormones and bile acids. Both dietary cholesterol and that synthesized de novo are transported through the circulation in lipoprotein particles. The same is true of cholesterol esters, the form in which cholesterol is stored in cells.

The synthesis and utilization of cholesterol must be tightly regulated in order to prevent over-accumulation and abnormal deposition within the body. Of particular importance clinically is the abnormal deposition of cholesterol and cholesterol-rich lipoproteins in the coronary arteries. Such deposition, eventually leading to atherosclerosis, is the leading contributory factor in coronary artery disease.

Cholesterol is minimally soluble in water; it cannot dissolve and travel in the water-based blood stream. Instead, it is transported in the blood stream by lipoproteins, i.e. protein "molecular-suitcases" which are water soluble and carry cholesterol and fats internally. The proteins form part of the surface of the given lipoprotein particle and determine from what cells cholesterol will be removed and where it will be supplied.

The largest lipoproteins, which primarily transport fats from the intestinal mucosa to the liver, are called chylomicrons. They carry mostly triglyceride fats and cholesterol (both from food and especially internal cholesterol secreted by the liver into the bile). In the liver, chylomicron particles give up triglycerides and some cholesterol and are converted into low-density lipoprotein (LDL) particles which carry triglycerides and cholesterol on to other body cells. In healthy individuals the low-density lipoprotein (LDL) particles are large and relatively few in number. Conversely, high numbers of small low-density lipoprotein (LDL) particles are strongly associated with promoting atheromatous disease within the arteries.

High-density lipoprotein. (HDL) particles transport cholesterol back to the liver for excretion, but vary considerably in their effectiveness for doing this. Having large numbers of large HDL particles correlates with better health outcomes. Conversely, having small amounts of large HDL particles is strongly associated with atheromatous disease progression within the arteries.

The cholesterol in LDL cholesterol and the cholesterol in HDL cholesterol are identical. The only difference between the two is the carrier protein molecules (i.e. the lipoprotein).

High cholesterol levels has been shown in many trials to be the source of cardiovacular disease. High cholesterol is the best known of all the many threats to a healthy heart. When excess amounts of this waxy, fat-like substance build up along the walls of the arteries, you face a dramatically higher risk of a complete blockage, leading to a heart attack or stroke.

At normal levels, cholesterol is not a bad thing. On the contrary, it's an essential raw material used by the body to build cell walls and produce hormones such as estrogen and testosterone. The body produces its own supply of cholesterol in the liver, and it's found naturally in all animal products (such as meats, eggs, milk, and cheese). It poses a problem only when the body is unable to use or eliminate excessive supplies.

As one of a variety of fatty substances in the body, cholesterol is classified as a lipid. It is carried through the bloodstream attached to proteins, forming complexes called lipoproteins. There are two major types of lipoproteins: the low-density lipoproteins (LDL) commonly known as "bad" cholesterol, and the high-density lipoproteins (HDL) usually dubbed "good" cholesterol. It's the "bad" LDL cholesterol that tends to form deposits on the artery walls. HDLs, on the other hand, help to clear excess cholesterol from the bloodstream. The ideal situation to aim for then, is a low level of LDL cholesterol, a high level of HDL cholesterol, and a moderate total of both.

The specific objective of this portion of the trial was to determine the effects of the supplement on blood lipid parameters. Significant reduction was noted in the overall LDL levels of the treatment group from day 0 to day 28. Perhaps what is more interesting is the increase in HDL levels, compared with a relative decrease in the placebo group.

However it is the ratios of various lipids and lipid proteins rather than the absolute values that are important in assessing cardiovascular risk, and consequently these ratios were calculated and tabulated.

A significant decrease in the ratio of TC/HDL, and in the ratio of LDL/HDL cholesterol in the supplement group was noted. A decrease in these ratios corresponds to an associated decrease in the risk of cardiovascular disease (CVD). These ratios are markers for a reduction in the risk of developing atherosclerosis. Consequently these results indicate that the supplement is very beneficial to for example the health of hypercholesterolemic individuals at risk of developing CVD.

As discussed above, there is provided a method of modifying blood lipid parameters comprising administering to an individual in need of such treatment an effective amount of the composition or supplement as described herein. As will be apparent to one of skill in the art, an effective amount of the supplement refers to the quantity thereof necessary to reduce the TC/HDL ratio or reduce the LDL/HDL ratio of an individual in need or desirous of such treatment and such dosages and regimens are enabled herein.

Specifically, as can be seen in table 2, the blood lipid parameters of those in the supplement group were modified in that total cholesterol was reduced by 5.3%, low density lipoprotein was reduced by 15% and HDL was increased by 4.3%. This is in stark contrast with the results observed for the control group fed the placebo, also shown in Table 2, wherein total cholesterol actually increased by 8.2%, LDL increased by 0.7% and HDL decreased by 4.7%.

As summarized on Table 3, the test group administered the supplement or composition showed a TC/HDL ratio reduced by 9.4% whereas the control or placebo group had an increased TC/HDL ratio of 1.7%. Similarly, the supplement group showed an LDL/HDL ratio decrease of 17.7% whereas the placebo or control group had only a 0.5% decrease. Finally, the supplement group showed a total glycerides to HDL increase of 3.0% whereas the control group showed a 20% increase.

Thus, administration of the supplement as described herein has been shown to reduce total cholesterol, increase HDL, decrease LDL, reduce the TC/HDL ratio and decrease the LDL/HDL ratio in test individuals compared to individuals administered a placebo or control. As such, the supplement can be used to reduce total cholesterol, increase HDL, decrease LDL, reduce the TC/HDL ratio and decrease the LDL/HDL ratio.

The supplement has an effect on immune parameters and, in particular, on basophil and possibly IL-6 levels. Given these changes, the supplement has the potential to substantially alleviate allergic responses.

The supplement could also have an effect in autoimmune diseases such as Crohn's disease or rheumatoid arthritis, or in the ability of subjects to resist the common cold virus.

This study verified that the supplement is effective in reducing circulating levels of LDL-cholesterol and increasing circulating levels of HDL cholesterol. It is of interest to note that there was a significant decrease in the ratio of TC/HDL, and in the ratio of LDL/HDL cholesterol, in the supplement group. A decrease in these ratios corresponds to an associated decrease in cardiovascular disease (CVD) risk, because these ratios are markers for a reduction in the risk of developing atherosclerosis.

While the preferred embodiments of the invention have been described above, it will be recognized and understood that various modifications may be made therein, and the appended claims are intended to cover all such modifications which may fall within the spirit and scope of the invention.

REFERENCES

International Journal of Immuno Pharmacology 1996 Vol 18 Bouic et al. Beta-sitosterol and beta-sitosterol glucoside, stimulate human peripheral blood lymphocyte proliferation; implications for their use as an immunomodulatory vitamin combination.
International Journal Molecular Medicine 2000 Vol 5 Awad et al. Inhibition of growth, and stimulation of apoptosis, by beta-sitosterol treatment of human breast cancer cells.
Anti Cancer Research 1998 Vol 18 (1 a) Awad, Holtz et al. Beta-sitosterol inhibits growth of HT-29 human colon cancer cells.
Nutrition and Cancer 1998 Vol 32 (1) von Holtz, Fink et al. Beta-sitosterol induces apoptosis in LNCaP human prostate cancer cells.
AIDS Bulletin 1997 Vol 6 Bouic. Immodulation in HIV/AIDS: The Tygerberg/Stellenbosch University Experience.
South African Journal of Science, 1997 Vol 93 Pegel. The Importance of Sitosterol and Sitosterolin in human and animal nutrition.
British Journal of Urology 1997 Vol 80 Klippel et al. A multi centric, placebo controlled, double blind clinical trial of betasitosterol for the treatment of benign prostatic hyperplasia.
The Lancet 1995 Vol 345 Berges et al. Randomized placebo controlled double blind clinical trial of beta-sitosterol in patients with benign prostatic hyperplasia.
The Arthritis Trust of America Summer 98 Bouic. Sterols/Sterolins the natural, none toxic immuno-modulators and their role in the control of rheumatoid arthritis.
Nutrition Reviews 1992 Vol 50 NO. 7 Block. The data support a role for antioxidants in reducing cancer risks.
Methods in Enzymology 1990 Vol 186 Bors, Heller et al. Flavanoids as anti-oxidants: determination of radical scavenging efficiencies.
The Lancet 1996 Vol 344 Cerruti. Oxi-radicals and cancer.
Biochemical Pharmacology 1990 Vol 39 No. 11 DeWhalley, Rankin et al. Flavanoids inhibit the oxidative modification of low density lipoproteins by macrophages.
The Lancet 1994 Vol 344 Grishan. Oxidants and free radicals in inflammatory bowel disease.
Phytochemistry 1987 Vol 26 No. 9 Husain, Cillard et al. Hydroxyl radical scavenging activity of flavanoids.
The Lancet 1994 Vol 344, Jenner. Oxidative damage in neuerodagenerative disease.
Free Radicals in Diagnostic Medicine, D. Armstrong, Plenum Press New York. Free radical scavenging and antioxidant activity of plant flavanoids.
New Zealand Journal of Science 1973 Vol 16 Markam and Porter. Extractives of pinus radiate bark-phenolic components.
New Zealand Journal of Science 1974 Vol. 17 Porter. Extractives of pinus radiate bark-procyanidin constituents.
Free radical Research 1995 Vol 22 No. 4 Rice-Evens, Miller et al. The relative antioxidant activities of plant derived polyphenolic flavanoids.
Biochemical Pharmacology 1998 Vol 37 No 5 Rbak, Gryglewski. Flavanoids are scavengers of super oxide anions.
Free Radical Biology in Medicine 1990 Vol 9 Yuting, Rongliang et al. Flavanoids as super oxide scavengers and antioxidants.

TABLE 1

The effects of supplement on specific immune parameters in experimental and placebo groups from day 0 to day 28

| Immune Parameter | Supplement Day 0 | Supplement Day 28 | Control Day 0 | Control Day 28 |
|---|---|---|---|---|
| IgE | 472.00 | 451.00 | 1335.00 | 1127.00 |
| DHEA | 6.44 | 6.44 | 4.93 | 4.77 |
| Cortisol | 507.00 | 584.00 | 490.00 | 498.00 |
| Cortisol/DHEA | 94.06 | 108.36 | 160.66 | 141.44 |
| IL-6 | 1.261 | 0.937 | 1.318 | 1.179 |
| WBC | 7.41 | 7.24 | 7.28 | 7.13 |
| Lymphocyte Segmented | 2.16 | 2.24 | 2.56 | 2.60 |
| Neutrophil | 4.65 | 4.39 | 4.11 | 3.97 |
| Monocytes | 0.33 | 0.34 | 0.35 | 0.31 |
| Eosinophils | 0.24 | 0.20 | 0.23 | 0.20 |
| Basophils | 0.23 | 0.01 | 0.13 | 0.04 |

TABLE 2

The effects of supplement on blood lipid parameters in
experimental and placebo groups from day 0 to day 28

| Blood Lipid Parameter | Supplement Day 0 | Supplement Day 28 | Control Day 0 | Control Day 28 |
|---|---|---|---|---|
| Total Cholesterol | 4.36 | 4.13 | 4.87 | 4.91 |
| LDL | 2.27 | 1.93 | 2.85 | 2.87 |
| HDL | 1.63 | 1.70 | 1.48 | 1.41 |
| TG | 1.00 | 1.09 | 1.18 | 1.38 |

TABLE 3

The effects of supplement on specific cardiovascular ratios in
experimental and placebo groups from day 0 to day 28

| Cardiovascular Parameter Ratios | Supplement Day 0 | Supplement Day 28 | Control Day 0 | Control Day 28 |
|---|---|---|---|---|
| TC/HDL | 2.88 | 2.61 | 3.50 | 3.56 |
| LDL/HDL | 1.58 | 1.30 | 2.11 | 2.10 |
| TG/HDL | 0.66 | 0.68 | 0.85 | 1.02 |

The invention claimed is:

1. A method of treating an allergy comprising administering to an individual in need of such treatment an effective amount of a composition consisting of:
   300 mg beta-sitosterols;
   50 mg essential fatty acid complexes;
   20 mg proanthocyanidins, flavonoids and polyphenols; and
   30 mg micro-cellulose filler.

2. The method according to claim 1 wherein the individual is in need of a reduction in basophil count and the effective amount is sufficient to reduce basophil count in said individual.

3. A method of treating an allergy in an individual in need of such treatment comprising administering to the individual an amount of a composition consisting of:
   300 mg beta-sitosterols;
   50 mg essential fatty acid complexes;
   20 mg proanthocyanidins, flavonoids and polyphenols; and
   30 mg micro-cellulose filler;
said amount being sufficient to reduce basophil count in said individual compared to a control.

* * * * *